(12) United States Patent
Frazier

(10) Patent No.: US 6,726,820 B1
(45) Date of Patent: Apr. 27, 2004

(54) METHOD OF SEPARATING BIOMOLECULE-CONTAINING SAMPLES WITH A MICRODEVICE WITH INTEGRATED MEMORY

(75) Inventor: Jeffery D. Frazier, Redwood City, CA (US)

(73) Assignee: Applera Corporation, Foster City, CA (US)

( * ) Notice: Subject to any disclaimer, the term of this patent is extended or adjusted under 35 U.S.C. 154(b) by 140 days.

(21) Appl. No.: 09/955,608

(22) Filed: Sep. 19, 2001

(51) Int. Cl.[7] ............................................. G01N 27/447
(52) U.S. Cl. ...................... 204/451; 204/450; 204/452
(58) Field of Search ................................. 204/450, 451, 204/461, 452, 603, 600, 601, 612

(56) References Cited

U.S. PATENT DOCUMENTS

| | | | |
|---|---|---|---|
| 4,908,112 A | | 3/1990 | Pace |
| 5,384,028 A | * | 1/1995 | Ito ............................. 257/253 |
| 6,013,168 A | * | 1/2000 | Arai ........................... 204/601 |
| 6,025,129 A | | 2/2000 | Nova et al. |
| 6,090,251 A | * | 7/2000 | Sundberg et al. ........... 204/453 |
| 6,258,606 B1 | | 7/2001 | Kovacs |
| 6,300,141 B1 | * | 10/2001 | Segal et al. .............. 435/287.1 |
| 6,454,924 B2 | * | 9/2002 | Jedrzejewski et al. ...... 204/601 |
| 6,458,259 B1 | * | 10/2002 | Parce et al. ................. 204/454 |

FOREIGN PATENT DOCUMENTS

WO  WO 01/47638 A2  7/2001

OTHER PUBLICATIONS

Translation of JP 2001–188,061A.*
Birge, "Protein–Based Three–Dimensional Memory—A light–absorbing molecule fro bacteria could provide faster access time and denser data storage in three–dimensional optical memories," *American Scientist*, 1994, pp. 348–355, vol. 82.
Birge et al., "Biomolecular Electronics: Protein–Based Associative Processor and Volumetric Memories," *J. Phys. Chem. B*, 1999, pp. 10746–10766, vol. 103.
Henke, "DNA–chip technologies—Part 1: Research fundamentals and industry catalysts," *IVD Technology Magazine*, 1998.
Henke, "DNA–chip technologies—Part 2: State–of–the–art and competing technologies," *IVD Technology Magazine*, 1998.
Henke, "DNA–chip technologies—Part 3: What dose the future hold," *IVD Technology Magazine*, 1998.
Frost, "Tiny Channels Carved in Plastic Enable Medical Tests on a CD," *Ohio State Research News*, 2000.

* cited by examiner

Primary Examiner—Kaj K. Olsen
(74) Attorney, Agent, or Firm—Kilyk & Bowersox P.L.L.C.

(57) ABSTRACT

The present invention provides microdevices, such as those used in the pharmaceutical and biotechnological fields, including an integrated memory. According to various embodiments, the integrated memory is readable, writable, and rewritable. The present invention further provides processing stations, e.g., for carrying out electrophoresis, pcr, genetic analysis, sample preparation, and/or sample cleanup, etc., that are capable of reading from and/or writing/rewriting to such memory.

11 Claims, 5 Drawing Sheets

METHOD OF SEPARATING BIOMOLECULE-CONTAINING SAMPLES WITH A MICRODEVICE WITH INTEGRATED MEMORY

FIELD OF THE INVENTION

The present invention relates to microdevices, such as those used in the pharmaceutical and biotechnological fields.

BACKGROUND OF THE INVENTION

In low-throughput situations, sample tracking and record keeping can often be handled adequately in a manual fashion. For example, one or several words about a sample, and/or an alphanumeric identifier, can be written or typed on a label that is applied to a container holding the sample. In some cases, additional (e.g., more detailed) information is kept in paper form, e.g., notebooks, and/or manually entered into a spreadsheet or database on a computing device, such as a personal computer (PC).

With the advent of medium- to high-throughput sample processing, it has become more challenging to track each sample and maintain information on it for ready accessing. Providing sample containers with bar codes has provided some advantages in sample tracking. As a practical matter, a bar code, per se, carries very little information, simply being an identifier. Further, there is a lower limit on the size of container with which a bar code can be used. In addition, a bar code itself is static information. That is, once a bar code is written and placed on a sample container, it cannot be readily changed.

Sample tracking and information maintenance will become even more challenging as the industry moves toward microdevice, very high-throughput formats.

In an effort to meet the challenges presented by very high-throughput sample processing, a great deal of effort has been focused on software and networking solutions to large-scale information management. It is envisioned that software and networking technologies will permit instruments and applications of all types to communicate with one another and to share database resources for tracking the many, many samples being processed. Many of today's popular commercial LIMS (laboratory information management systems), for example, are moving toward the use of open systems architectures and platforms to offer client/server capabilities and enterprise-wide access to lab information.

Notwithstanding the advantages offered by such LIMS, it will happen that a sample, or many samples in a microdevice, will need to be physically transported between sites, machines and/or computers that are not connected by a network or LIMS.

SUMMARY OF THE INVENTION

Aspects of the invention provide a microdevice including a memory integrated into the microdevice. The memory can be, for example, a readable-writable-rewritable memory (also referred to herein simply as a "rewritable" memory).

Further aspects of the invention provide a sample-processing station (e.g., for genetic analysis, electrophoresis, pcr, sample preparation and/or sample cleanup, etc.) configured for reading from, and/or writing/rewriting to, the memory integrated into a microdevice.

A wide variety of information can be written to the memory of a microdevice. For example, sample ID, sample history, sample lineage, a person's notes pertaining to a sample, etc. In various embodiments, a memory that is integrated into a substrate defining, at least in part, a microdevice carries instructions that can be read by an apparatus for acting on samples held by the microdevice, which the apparatus can read and carry out. Optionally, the apparatus can then write to the memory of the microdevice (e.g., results pertaining to the act(s) performed, etc.).

A microdevice of the invention can be transported from one place to another, and the memory accessed at each location. The information (written to the integrated memory) and the microdevice (including any sample(s) therein) can conveniently be transported and/or stored (etc.) as a unit.

A microdevice of the present invention can find use alone, or in combination with one or more other sample tracking and information storage/retrieval technologies, such as those previously discussed.

Among other things, the present invention provides advancements in methods and devices for tracking samples, and/or storing and retrieving information pertaining thereto. Such advancements can be used as an alternative or a supplement to known methods and devices, such as those previously discussed.

Aspects of the invention provide a microdevice, various embodiments of which comprise a substrate or body, such as a plate, wafer, chip, slide, disc, or the like, including one or more microfluidic structures (e.g., channels, wells, chambers, reservoirs, or any combination thereof), and a readable-writable-rewritable memory integrated into the substrate, with the memory being adapted for storing binary coded information.

In various embodiments, at least one of the one or more microfluidic structures comprises a channel having a cross-sectional dimension of no greater than 500 micrometers (e.g., no greater than 250 micrometers, no greater than 100 micrometers, or no greater than 75 micrometers).

According to various embodiments, one or more of the microfluidic structures comprises a chamber, well or reservoir configured to hold a micro-volume of a fluidic sample, the micro-volume being no more than about 250 $\mu$l (e.g., about 100 $\mu$l, 75 $\mu$l, 50 $\mu$l, or less).

According to various embodiments, the integrated memory can be permanently fixed in or to the substrate, or it can be removably attached to the substrate.

In various embodiments, the memory is selected from the group consisting of integrated circuit memories, optical memories, thin film semi-conductor memories, ferromagnetic memories, molecular memories, biomolecular memories, and any combination thereof.

Various embodiments further include a microcontroller chip supported by (e.g., integrated into) the substrate and adapted for communication with the memory.

In various embodiments, machine-readable computer code is stored in the memory.

According to various embodiments, at least one read-only memory is also integrated into the substrate.

Further aspects of the invention provide an electrophoresis microdevice, various embodiments of which comprise a substrate including one or more microscale structures configured to support one or more fluidic samples; and a readable-writable-rewritable memory integrated into the substrate.

According to various embodiments, an electrophoresis microdevice can further include (i) one or more electrodes (e.g., microelectrodes integrated into the substrate), and (ii)

a power source (e.g., a DC power source); with the one or more electrodes being connectable to the power source to generate one or more electrical fields along at least one of the one or more microscale structures.

In another of its aspects, the present invention provides a thermal cycling microdevice, various embodiments of which include a substrate including one or more microscale structures (e.g., wells or reservoirs) adapted to receive or support one or more biomolecule-containing samples (e.g., DNA-containing samples); a readable-writable-rewritable memory integrated into a region of the substrate; and a temperature control element or device, adapted to modulate (cycle) the temperature within at least one of the one or more microscale structures.

Another aspect of the present invention provides an apparatus for acting on one or more biomolecule-containing samples supported by a microdevice, such as a microdevice including an integrated readable-writable-rewritable memory. In various embodiments, an apparatus includes: a housing; a reader-writer unit mounted in the housing, with the reader-writer unit being adapted to receive a region of the microdevice into which the memory is integrated; and a support mounted in the housing, for holding the microdevice while the samples are acted upon and while the memory region is received within the reader-writer unit.

According to various embodiments, an apparatus further includes a detector operably coupled to a region whereat a microdevice is located when held by the support.

In various embodiments, an apparatus further comprises a temperature control module adapted to regulate the temperature of at least a portion of a microdevice when held by the support.

According to various embodiments, an excitation-beam source (e.g., a laser) is configured to direct an excitation beam of light along an optical path leading to a region whereat a microdevice is located when held by the support.

Further aspects of the present invention provide a system for acting on samples, and storing and retrieving information pertaining thereto. According to various embodiments, the system comprises: a microdevice including one or more microfluidic structures adapted to support at least one biomolecule-containing sample; a readable-writable-rewritable memory integrated into the microdevice; and a reader-writer unit adapted to receive the memory and to read from, and write/rewrite to, the memory.

In various embodiments, a system further includes a sample-processing station; with the reader-writer unit being mounted in the station.

According to various embodiments, the memory of a system has a storage capacity of at least 500 kilobytes (e.g., at least 1 megabyte, at least 10 megabytes, at least 100 megabytes, or greater).

In another of its aspects, the present invention provides a method for acting on one or more fluidic samples, and storing and retrieving information pertaining thereto. In various embodiments, a method comprises: (i) providing a microdevice comprising a substrate including one or more microfluidic structures, and a readable-writable-rewritable memory integrated into the substrate; (ii) manipulating one or more fluidic samples in the microfluidic structures; and (iii) storing binary coded information in the memory pertaining to the one or more samples.

In various embodiments, the one or more microfluidic structures are selected from the group consisting of channels, chambers, wells, reservoirs, and any combination thereof.

According to various embodiments, the manipulating step comprises electrophoresing at least one of the one or more fluidic samples.

In various embodiments, the one or more fluidic samples includes one or more polynucleotides. Additionally, the manipulating step can comprise amplifying at least one of the one or more polynucleotides (e.g., by polymerase chain reaction (pcr)).

According to various embodiments, at least 500 kilobytes (e.g., at least 750 kilobytes, at least 1 megabyte, at least 10 megabytes, or more) of information is stored in the memory.

Further aspects of the present invention provide a microdevice, various embodiments of which comprise a substrate including means for supporting one or more biomolecule-containing samples; and means for storing binary coded information integrated into the substrate.

In various embodiments, the means for storing includes a storage capacity of at least 500 kilobytes (e.g., at least 750 kilobytes, at least 1 megabyte, at least 10 megabytes, or more).

According to various embodiments, the means for storing comprises a readable-writable-rewritable memory structure.

BRIEF DESCRIPTION OF THE DRAWINGS

The structure and manner of operation of the invention may further be understood by reference to the following description taken in conjunction with the accompanying drawings, in which identical reference numerals identify identical or similar elements, and in which.

DESCRIPTION OF THE INVENTION

Figure 1:
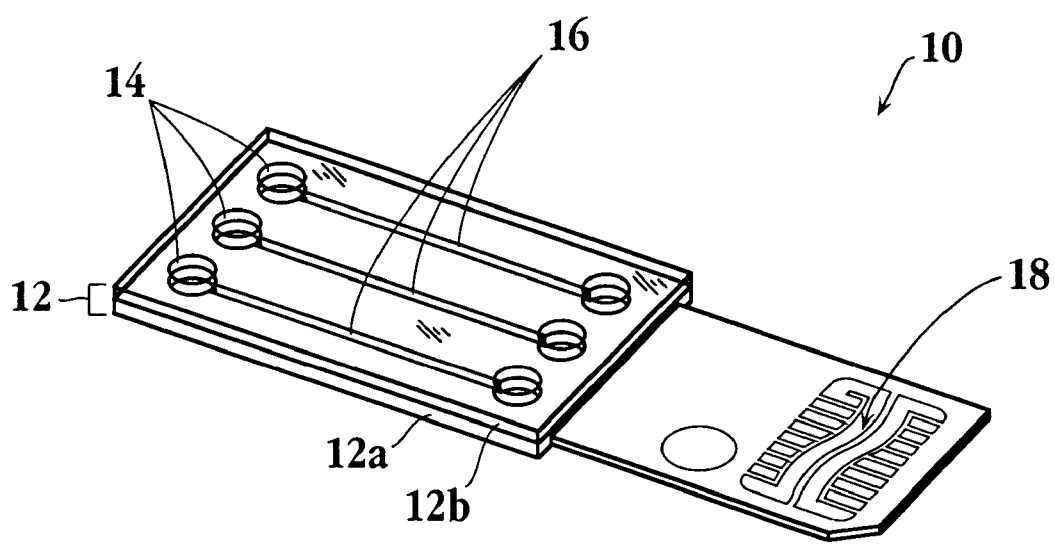
FIG. 1 is a perspective view of a microdevice including an integrated memory, in accordance with the teachings herein.

Reference will now be made to various embodiments of the invention, examples of which are illustrated in the accompanying drawings. While the invention will be described in conjunction with various embodiments, it will be understood that they are not intended to limit the invention. On the contrary, the invention is intended to cover alternatives, modifications, and equivalents, which may be included within the invention as defined by the appended claims.

Aspects of the invention provide a microdevice including one or more memory structures integrated into the microdevice. Further aspects of the invention provide a sample processing station configured for reading from and/or writing/rewriting to the memory of a microdevice.

As used herein, the term "integrated" refers to a configuration wherein memory is fabricated into the body structure of a microdevice, or is attached to the body structure, such that the memory and body structure form a single integrated unit. The attachment can be permanent, or the memory can be removably attached to the body structure. In an embodiment of the latter, the memory is securely attached to the body structure until such time that a user should decide to remove it (e.g., one or more memory chips can be removably snap-fit to appropriately configured regions of the body structure).

A typical microdevice includes a substrate or body structure that has one or more microscale sample-support, manipulation, and/or analysis structures, such as a channel, well, chamber, reservoir, valve or the like disposed within it. As used herein, "microscale" refers to a fluid channel or conduit that has at least one cross-sectional dimension, e.g., width, depth or diameter, of no greater than about 1 micrometer. In various embodiments, such channels have at least one cross-sectional dimension of no greater than 750 micrometers, and in certain embodiments, from 1 to 500 micrometers (e.g., between 5 to 250, or between 5 to 100, micrometers). In one embodiment, a microscale channel has at least one cross-sectional dimension of between about 10–75 micrometers. With respect to chambers or wells, "microscale," as used herein, refers to structures configured to hold a small (micro) volume of fluid; e.g., no greater than 250–300 $\mu$l. In various embodiments, such chambers are configured to hold no more than 100 $\mu$l, no more than 75 $\mu$l, no more than 50 $\mu$l, no more than 25 $\mu$l, no more than 1 $\mu$l, or no more than 50 $\mu$l (e.g., about 30 $\mu$l).

A microdevice can be configured in any of a variety of shapes and sizes. In various embodiments, a microdevice is generally rectangular, having a width dimension of no greater than about 15 cm (e.g., about 2, 6, 8 or 10 cm), and a length dimension of no greater than about 30 cm (e.g., about 3, 5, 10, 15 or 20 cm). In other embodiments a microdevice is generally square shaped. In still further embodiments, the substrate is generally circular (i.e., disc-shaped), having a diameter of no greater than about 35 cm (e.g., about 7.5, 11.5, or 30.5 cm). The disc can have a central hole formed therein, e.g., to receive a spindle (having a diameter, e.g., of about 1.5 or 2.2 cm). Other shapes and dimensions are contemplated herein, as well.

Chip, wafer, and plate devices (e.g., genetic analysis microdevices, microchannel electrophoresis devices, pcr chips, $\mu$TAS devices, lab-on-a-chip systems, sample preparation/cleanup devices, etc.), spinning disc substrates (e.g., those developed by Gyros and Gamera), and biomolecule array chips (e.g., those developed by Hyseq and Affymetrix) have been the subjects of intensive R&D efforts. Such devices generally permit many operations to be performed at once on a large number of samples (e.g., tens, hundreds, thousands, tens of thousands, or more), with the samples all being the same or substantially the same, all being different from one another, or some combination thereof. The present invention combines such structures with a portable or small-scale memory format; and in various embodiments, a readable, writable, and/or rewritable memory (or simply, a "rewritable" memory).

The present teachings are particularly well suited for microfluidic devices. The term "microfluidic" refers to a system or device having channels, chambers, wells, and/or reservoirs (e.g., a network of chambers and/or wells connected by channels) for supporting or accommodating very small (micro) volumes of fluids, and in which the channels, chambers, wells, and/or reservoirs have microscale dimensions. See, e.g., U.S. Pat. Nos. 6,132,685, 6,103,199, 6,054,277, and 6,033,546; and EP 1003759; and WO 0126812, WO 0076662, and WO 9850154; each incorporated herein by reference.

A variety of memory structures permitting integration into a microdevice can be utilized herein, e.g., integrated circuit memories, optical memories, thin film semi-conductor memories, ferromagnetic memories (e.g., magnetic stripe memories; see, e.g., U.S. Pat. No. 4,281,396; incorporated herein by reference), molecular memories (see, e.g., U.S. Pat. No. 6,256,767, incorporated herein by reference), and biomolecular memories (e.g., storage devices based upon conformational states of organic molecules, such as bacteriorhodopsin (BR); see, e.g., Birge et al., Biomolecular electronics: Protein-based associative processors and volumetric memories, J. Phys. Chem. B. 103, 10746–10766 (1999); and Birge, R., "Protein-Based Three-Dimensional Memory," American Scientist, July-August 1994, pp. 348–355; each incorporated herein by reference), etc.

Thanks in large part to the widespread acceptance and use of digital cameras, mobile computing devices, personal music players, etc., small-format memory devices have become well developed in recent years. Memory cards, such as flash cards, and portable discs, such as readable-writable-rewritable CDs and DVDs, are gaining wide use. These, and other, small-format memory devices can be employed herein.

According to various embodiments, a microdevice is provided with, for example, a memory of a type that can store information even when there is no power supplied to it. For example, a microdevice can include a flash memory; e.g., the flash technology utilized in commercial products such as CompactFlash™ (by SanDisk), MemoryStick™ (by Sony), SmartMedia™ (by Toshiba), etc. In brief, a typical flash memory, for example, includes flash memory chips and a microcontroller chip that manages the storage of digital information (images, data, voice, etc.) and electronic interfacing. Flash memory is a nonvolatile silicon memory, meaning that no battery power is required to keep the digital information stored on the card literally for hundreds of years without deterioration of information quality. See, for example, U.S. Pat. Nos. 6,252,791, 5,172,338, 5,663,901, 5,747,359, 5,887,145; and 6,199,122; each of which is incorporated herein by reference.

It should be appreciated that flash-memory devices are merely one category of memory that can readily be incorporated into a microdevice, as taught herein, and that the invention is not limited to flash memory, but includes a variety of small-format or portable memory structures capable of being integrated into a microdevice.

In various embodiments, the memory is adapted for storing binary coded information (see, e.g., U.S. Pat. Nos. 4,905,189, 4,477,739, 5,923,583; 4,831,584; each incorporated herein by reference).

An integrated memory, as contemplated herein, can be configured with a variety of storage capacities. In various embodiments, for example, a microdevice of the invention includes an integrated memory having a storage capacity of at least 250 kilobytes (kb), at least 500 kb, at least 750 kb, at least 1 megabyte (Mb), at least 10 Mb, at least 100 Mb, at least 250 Mb, at least 500 Mb, and/or at least 1 Gigabyte (Gb), or higher.

Microscale sample-support, manipulation, and/or analysis structures (e.g., channels, chambers, wells, reservoirs, valves, micro-electronics such as electrodes, etc.) can be formed in or on a substrate, such as a plate, slide, wafer, chip, disc, or the like, by fabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. For example, Backhouse et al., DNA sequencing in a monolithic microchannel device, Electrophoresis 2000, 21, 150–156; Dolnik et al., Capillary electrophoresis on microchip, Electrophoresis 2000, 21, 41–54; Woolley et al., Ultra-high-speed DNA fragment separations using microfabricated capillary array electrophoresis chips, Proc. Natl. Acad. Sci., vol. 91, pp. 11348–11352, November 1994; and Madou, Fundamentals of Microfabrication, CRC Press, Boca Raton, Fla. (1997) (each of which is incorporated herein by reference) discuss certain microfabrication techniques that the skilled artisan can employ in making microdevices.

In various embodiments, separation channels are formed in a generally planar substrate comprised at least in part, for example, of an electrically insulating material, e.g., fused silica, quartz, silicate-based glass, such as borosilicate glass, phosphate glass, alumina-containing glass, and the like, or other silica-like material(s). According to some embodiments, separation channels are formed in a plastic substrate.

One suitable channel microdevice for use in the present invention is the Standard Microfluidic Chip (Simple Cross, MC-BF4-SC) from Micralyne Inc. (Edmonton, Alberta, Canada). Multiple cross-channel or other channel arrangements can be provided on a single chip or plate, as desired.

A channel microdevice, as contemplated herein, can include no more than one channel, or can include a plurality of channels, e.g., at least 5, 10, 15, 20, 25, or more channels. In an embodiment, a microdevice for analyte separation includes at least 5, 10 or 15 separation channels.

In the exemplary arrangement of FIG. 1, a microdevice 10 comprises a substrate (or body) 12 in which sample chambers 14 and channels 16 are formed (e.g., microfabricated), with a chamber or reservoir provided in fluid communication with each end of each channel. More particularly, substrate 12 is comprised of lower and upper plates, 12a and 12b respectively, with abutted confronting faces. Lower plate 12a is provided with elongate grooves, each of roughly semi-circular or semi-oval cross section, that in part define boundaries for channels 16. The lower face of upper plate 12b is substantially planar, and, when disposed against lower plate 12a as shown, further defines boundaries for channels 16. Particularly, in the illustrated arrangement, the grooves of plate 12a define lower (floor) and sidewalls or boundaries of each channel 16 and the lower surface of plate 12b provides an upper wall or ceiling (boundary) for channels 16. Through-holes can be formed through upper plate 12b to provide access to, and to define in part, the chambers 14.

Lower plate 12a of substrate 12 includes a region, as at 18, incorporating readable-writable-rewritable memory, such as flash memory. Memory region 18, in this embodiment, is configured as an outwardly extending projection, in the plane of lower plate 12a, so that upper plate 12b does not cover it. The projection can be configured in a variety of ways. In various embodiments, for example, the projection is provided with the shape of a standard PCMCIA card (also known as a PC card).

Figure 2:
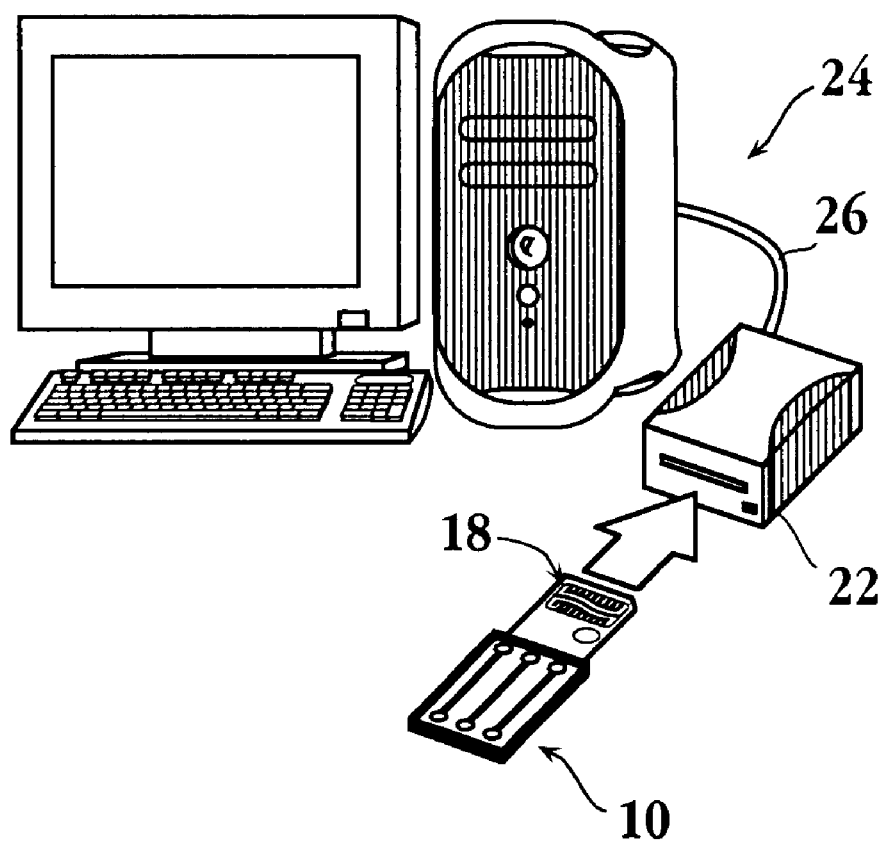
FIG. 2 is a perspective view of a microdevice including a memory region configured for insertion into a computer-connected reader-writer unit, in accordance with the teachings herein.

According to various embodiments, and with reference to the exemplary arrangement of FIG. 2, the memory region 18 of a microdevice 10 can be configured so as to be insertable into a reader-writer unit 22. The reader-writer unit 22 can be adapted for communication with a computing device, such as shown at 24, via a USB or FireWire connection 26. The memory can be written to before, during and/or after processing.

Small-format memory reader-writer units are well known (see, e.g., U.S. Pat. Nos. 6,149,058; 6,125,405; 6,223,984; JP 10320508; and WO 0067098; each incorporated herein by reference). Such known units can readily be adapted for use herein.

Figure 3:
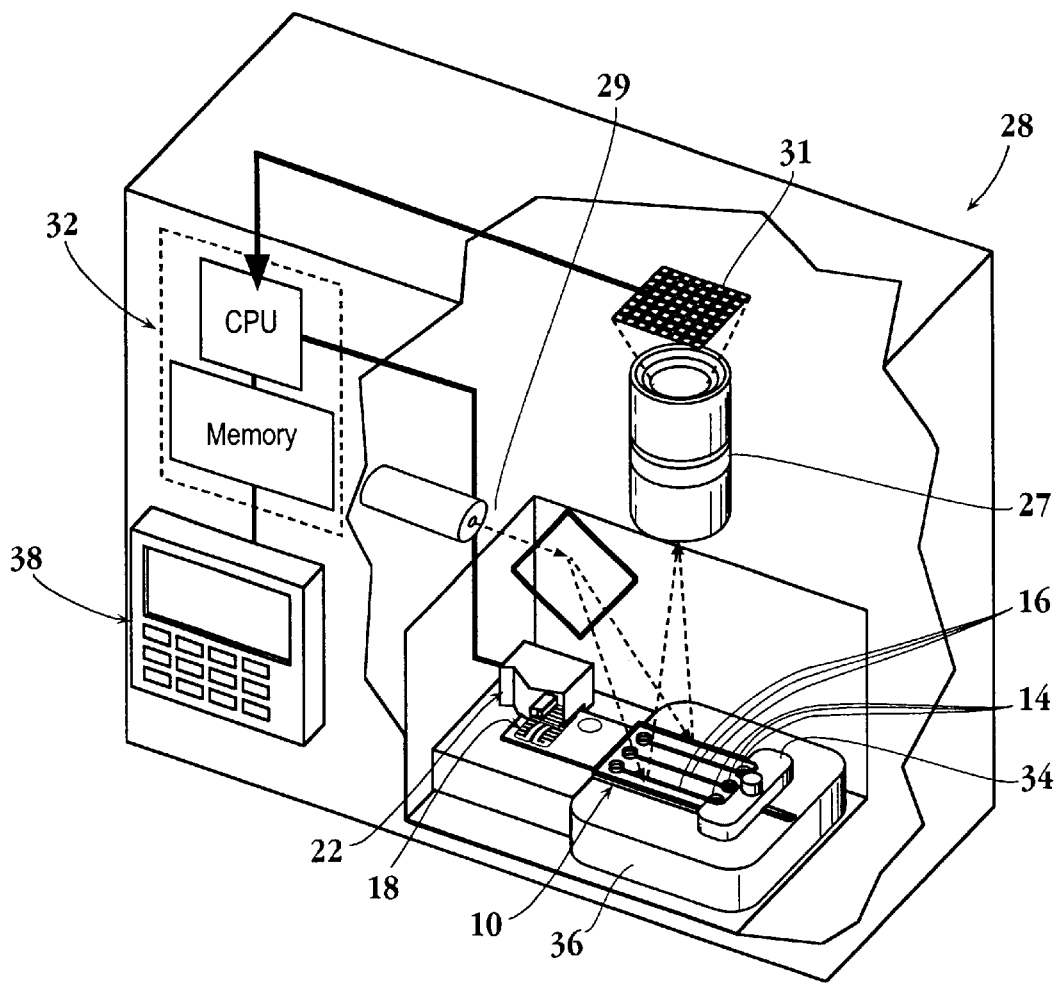
FIG. 3 is a partially schematic, perspective view, with portions broken away, of a reader-writer unit incorporated in a sample-processing station, permitting data to be read, written, and/or rewritten while a microdevice is operably mounted in the station, in accordance with the teachings herein.

According to various embodiments, and with reference to the exemplary arrangement of FIG. 3, a reader-writer unit 22 is incorporated in an apparatus or station 28 configured to carry out sample processing, such as an automated electrophoresis apparatus, so that data can be read, written, and/or rewritten while a microdevice 10 is operably mounted in the processing station 28. The processing station 28 can include integrated computing capabilities 32 programmed for receiving and processing data (alternatively, or in addition, the station 28 can be operably linked to an external computing device, such as a Macintosh or PC, and/or to a display-capable input-output device). In the illustrated embodiment, a human interface device is provided comprising an externally accessible keypad input/output unit with an LCD display, shown at 38. A variety of information, such as results or output generated from use of the station, can then be written to the integrated memory 18 of the microdevice 10. If desired, the microdevice can be transported to another computer, computing-capable processing station, or other desired location, where the stored information can be accessed, etc. Certain embodiments contemplate storing the microdevice in a safe place, so as to archive information held in the integrated memory.

In some embodiments, a microdevice is configured as a single or limited-use, disposable unit.

Various embodiments are particularly adapted to biomolecule (e.g., DNA, RNA, etc.) sequence or other analysis methods, in which each of a plurality of different fragment types is labeled with a spectrally distinctive fluorescent dye. For example, with continued reference to FIG. 3, processing station 28 can include a support 34 for mounting a microdevice 10 (here, the microdevice being a multi-channel electrophoresis device having a plurality of electroseparation channels). A thermal control module 36, e.g., Peltier-effect heat-transfer devices, is provided for regulating the temperature of the microdevice 10. A laser 29 is adapted to direct an excitation beam of light at a detection zone at a location along one or more separation channels 16 of the microchannel electrophoresis device 10. The excitation beam excites the dyes to emit light. Emitted light from sample zones passes through a collection lens, through a laser light filter, and through a focusing lens, indicated collectively at 27. The focused light is incident on a detector array 31 (e.g., a CCD) capable of detecting the emissions from the detection zone. Electronic signals from the detector array can provide information about the character or sequence of the biomolecule sample. Such information can be written by a reader-writer unit 22 to an integrated memory 18 of the device 10.

In one arrangement, two programs are installed on the computing portion 32 of the processing station 28, or on the linked computer, that can collect and analyze data produced by a micro-channel plate sequencer: (i) a data collection program ("Data Collection") and (ii) a sequencing analysis program ("Analysis"). Data Collection processes the information as it is generated and plots the four different emission signals (corresponding to the four nucleotides) over time during runs. After the runs are finished, the Data Collection program launches the Analysis program. Analysis integrates the raw data, normalizes the spacing, enhances the signal peaks, and uses this information to determine the parameters for calling the bases. The analyzed data are re-plotted together as a series of color peaks representing the nucleotide sequence (i.e., a chromatogram or electropherogram). The results are stored in a Sample File, which includes the raw data, the chromatogram, the nucleotide sequence, and the file information entered by the user. A second file that contains the sequence as text only is also generated for each sample. This sequence text file is suitable for use in other applications (e.g., database searches). See Hagemann et al., ABI Sequencing Analysis, Molecular Biotechnology, Vol. 13, 137–152 (1999); incorporated herein by reference. Any one or more of the files can be written to the memory region 18 of the microdevice 10.

It should be appreciated that the memory of the microdevice can store a variety of types of information, including software applications and/or operation instructions that can be loaded to, and executed by, a computing device, such as a computing capable processing station or a desktop computer. In embodiments employing a rewritable storage medium, the stored information can reflect, for example, changes in, or processing steps performed on, one or more samples; sample lineage; plate creation; sample logging; location management; etc.

Optionally, a microdevice including an integrated memory can further include an integrated microprocessor for executing instructions (code) on-board. In various embodiments, in addition to readable-writable-rewritable memory, the microdevice further includes integrated memory storing one or more software applications and/or operating instructions that can operate on or otherwise utilize information (e.g., data) written to the readable-writable-rewritable memory of the device. The additional memory can also be readable-writable-rewritable memory, or it can be read-only memory (ROM).

Figure 4:
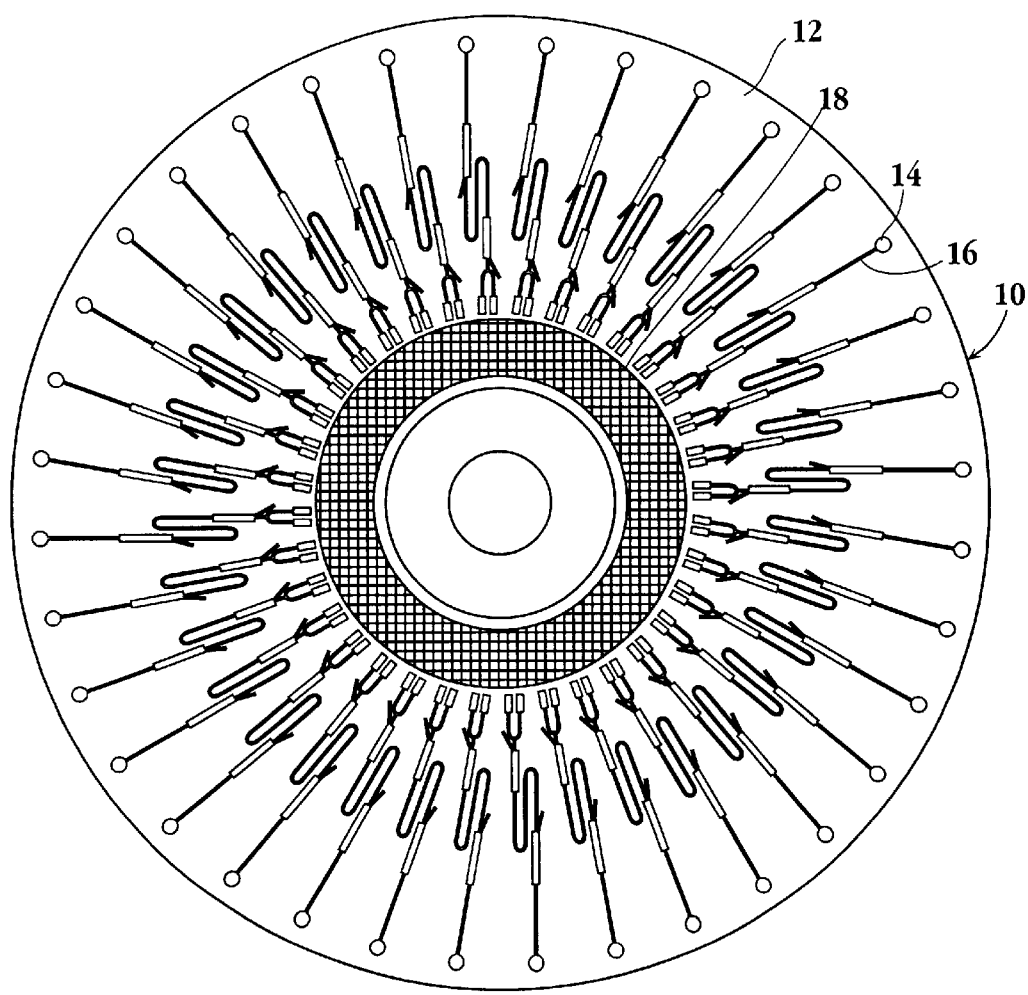
FIG. 4 is a partially schematic view of one face of a disc-type microdevice including a plurality of microfluidic structures, such as channels, chambers, etc., and a readable-writable-rewritable memory region, in accordance with the teachings herein.

In a spinning disc microdevice, an example of which is indicated at 10 in FIG. 4, a region of a disc-like substrate 12 is configured as a readable, writable, re-writable memory 18 (e.g., employing, for example, memory structures as used in CDs or DVDs). Information can be read, written and/or rewritten as the device is spinning. This can take place before, during and/or after sample processing. While exemplary channel 16 and chamber 14 structures are shown in FIG. 4, it should be appreciated that a variety of microscale structures can be utilized.

A variety of spinning disc substrates can be utilized herein. For example, micro-machined CD-type biomedical devices have been developed that may be used, for example, to analyze blood gases and blood electrolytes. Machining options for fluidic channels with diameters greater than 80 μm include direct CNC machining in plastic and plastic molding from a metal master (itself made by CNC machining). With dimensions below 80 μm, lithography techniques can be used. In some such devices, the intelligence in the structure resides in the dependence of the opening of various valves on rotation speed; the faster the disc spins, the smaller the capillaries that can be accessed by the fluids. The operating principles of certain centrifugal-based fluidic platforms are described in more detail, for example, in WO 0040750, WO 0147638, and WO 9853311; each incorporated herein by reference.

Reader-writer units and readable-writable-rewritable optical media, such as CD (e.g., CD-RW) and DVD (e.g., DVD-RW) type media, are well known (see, e.g., U.S. Pat. No. 5,459,707; 5,508,988; 5,465,245; 6,266,303; 5,514,440; EP 0871160; EP 0880780; EP 1091358; each incorporated herein by reference). Such known units and media can readily be adapted for use herein.

Figure 5:
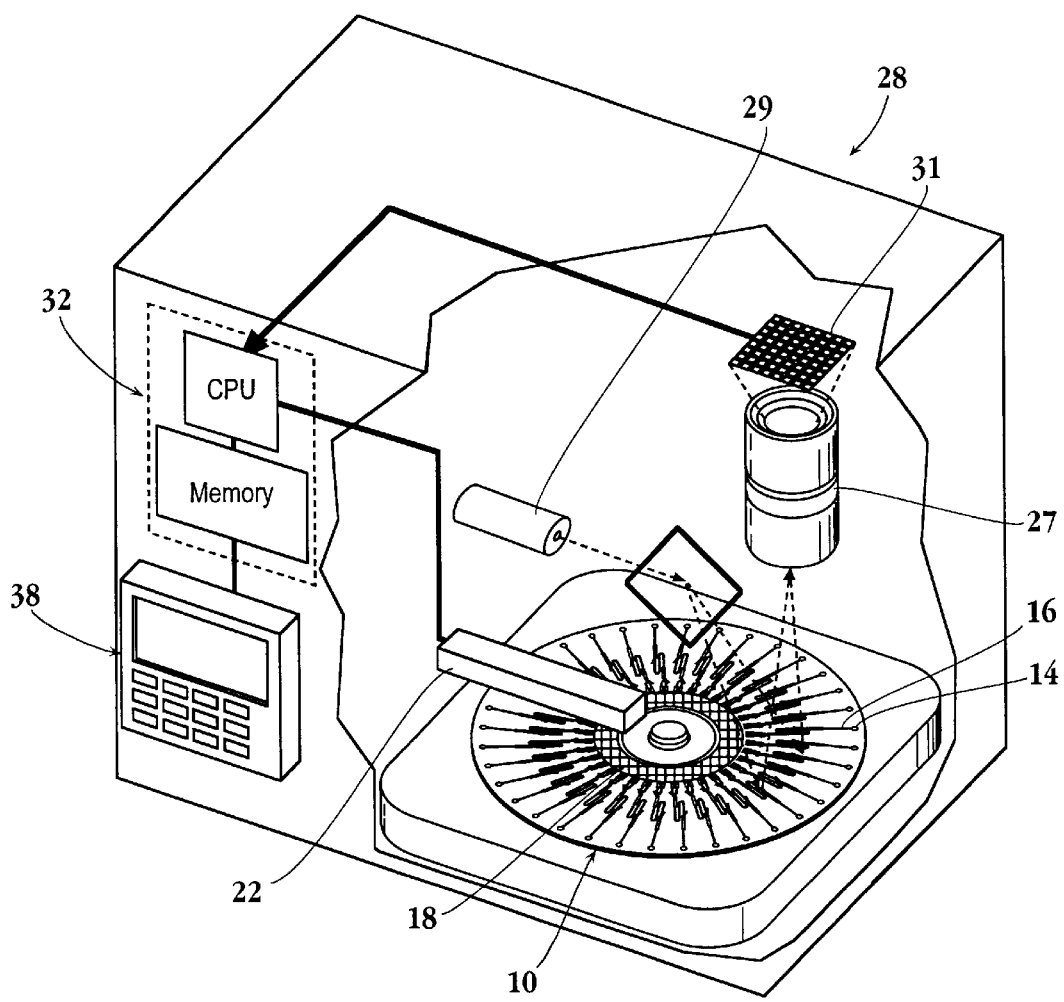
FIG. 5 is a partially schematic, perspective view, with portions broken away, of a reader-writer unit incorporated in a sample-processing station, permitting data to be read, written, and/or rewritten while a spinning-disc microdevice is operably mounted in the station, in accordance with the teachings herein.

FIG. 5 is a partially schematic, perspective view, with portions broken away, of a reader-writer unit 22 incorporated in a sample-processing station 28, permitting data to be read, written, and/or rewritten while a spinning-disc microdevice 10 is operably mounted in the station. Other components shown in FIG. 5 are substantially as described with respect to FIG. 3.

It is contemplated that a variety of types of microdevice can be configured with a readable-writable memory, in accordance with the teachings herein. For example, pcr-capable microdevices (such as disclosed in WO 0134842; U.S. Pat. Nos. 6,261,431; 6,203,683; each incorporated herein by reference); electrophoresis microdevices (such as disclosed in U.S. Pat. Nos. 6,261,430; 6,045,676; and pending U.S. patent application Ser. No. 08/726093 filed Oct. 4, 1996; each incorporated herein by reference); polynucleotide array microdevices (e.g., the GeneChip™ from Affymetrix, the HyChip™ from Hyseq, and devices such as disclosed in U.S. Pat. Nos. 5,445,934; 5,837,832; EP 1047794; each incorporated herein by reference); concentration, purification and/or clean-up microdevices (such as disclosed in U.S. Provisional Patent Application Serial No. 60/288268 filed May 2, 2001; U.S. Provisional Patent Application Serial No. 60/318269 filed Sep. 7, 2001; U.S. pat. No. 5,726,026; and WO 9933559; each incorporated herein by reference); spinning-disc-type microdevices (such as disclosed in WO 0040750, WO 0147638, and WO 9853311; each incorporated herein by reference); μTAS devices (such as disclosed in U.S. Pat. Nos. 6,194,900; 5,571,410; WO 0058724; each incorporated herein by reference); microelectromechanical system (MEMS) devices (such as disclosed in U.S. Pat. Nos. 6,116,863; 5,909,069; 5,710,466; and U.S. Pat. No. 5,655,665; each incorporated herein by reference); to name a few.

All publications and patent applications referred to herein are hereby incorporated by reference to the same extent as if each individual publication or patent application was specifically and individually indicated to be incorporated by reference.

Those having ordinary skill in the electrophoresis art will clearly understand that many modifications are possible in the above preferred embodiments without departing from the teachings thereof. All such modifications are intended to be encompassed within the following claims.

What is claimed is:

1. A method for separating biomolecule-containing samples, comprising:
   (a) providing a microdevice comprised of (i) a substrate; (ii) a separation channel formed in said substate, (iii) a rewritable memory integrated into said substrate, with said memory being adapted for storing binary coded information;
   (b) introducing a biomolecule-containing sample into said separation channel;
   (d) applying a driving force sufficient to cause at least a portion of the biomolecules in said sample to migrate along said separation channel, thereby separating the biomolecules;
   (e) detecting for the biomolecules; and (f) storing information in said memory about a character or a sequence of said biomolecules.

2. The method of claim 1, wherein said substrate comprises a plate, wafer, chip, slide, or disc.

3. The method of claim 1, wherein said driving force comprises an electric field.

4. The method of claim 1, wherein said driving force comprises a centrifugal force.

5. The method of claim 1, further comprising:

transporting the substrate from a first location to a second location; and accessing the rewritable memory at the first location and accessing the rewritable memory at the second location.

6. The method of claim 1, further comprising storing the microdevice, including the biomolecule-containing sample therein, as a unit.

7. The method of claim 1, wherein the microdevice further comprises one or more electrodes each capable of being connected to a power source, the one or more electrodes being disposed with respect to at least one of said separation channels for generating one or more electrical fields along at least a portion thereof.

8. The method of claim 1, wherein the microdevice comprises a plurality of separation channels and said separation channels are non-intersecting.

9. The method of claim 1, wherein the rewritable memory is permanently affixed to the substrate.

10. The method of claim 1, wherein the rewritable memory comprises at least one of an integrated circuit memory, an optical memory, a thin film semiconductor memory, a ferromagnetic memory, a molecular memory, and a biomolecular memory.

11. The method of claim 1, wherein said memory includes a storage capacity of at least 1 megabyte.

* * * * *

UNITED STATES PATENT AND TRADEMARK OFFICE
CERTIFICATE OF CORRECTION

PATENT NO. : 6,726,820 B1
DATED : April 27, 2004
INVENTOR(S) : Jeffery D. Frazier It is certified that error appears in the above-identified patent and that said Letters Patent is hereby corrected as shown below:

<u>Column 10,</u>
Line 57, replace "substate" with -- substrate --.

Signed and Sealed this

Twenty-sixth Day of July, 2005

JON W. DUDAS
*Director of the United States Patent and Trademark Office*